United States Patent [19]

Sabelli

[11] Patent Number: 5,455,276
[45] Date of Patent: Oct. 3, 1995

[54] METHOD FOR TREATING DEPRESSION

[76] Inventor: Hector C. Sabelli, 2400 Lakeview, #2802, Chicago, Ill. 60614

[21] Appl. No.: 64,222

[22] Filed: May 20, 1993

[51] Int. Cl.⁶ ............................................. A61K 31/135
[52] U.S. Cl. ........................ 514/655; 514/654; 514/649; 514/328
[58] Field of Search .................................. 514/654, 649, 514/328, 655

[56] References Cited

U.S. PATENT DOCUMENTS 4,421,767  12/2083  Palfreyman et al. .................... 424/319
4,705,796  11/1987  Hendry et al.
4,880,833  11/1989  Knoll et al.

OTHER PUBLICATIONS

Birkmayer et al., *Medline Abstrcts*, No. 84187532, 1984.
Reynolds et al., *Medline Abstracts*, No. 79131749, 1978.
Mann et al., *Medline Abstracts*, No. 89087241, 1989.
Piccinin et al., *Medline Abstracts*, No. 90227672, 1990.
Liebowitz et al., *Medline Abstracts*, No. 85175264, 1985.
Timar et al., *Chemical Abstracts*, vol. 104, No. 23, Jun. 9, 1986, abstract no. 200153e.
Beck, et al., *Beck Depression Inventory* (Harper & Row Publishers, Inc. 1961).
Boulton, et al., *Br. J. Pharmacol.*, 59:209–214 (1977).
DeLisi, et al., *Psychiat. Res.*, 13:193–201 (1984).
Durden and Philips, *J. Neurochem.*, 34:1725–1732 (1980).
Fischer, et al., *Acta Physiol. Lat. Amer.*, 17:15–21 (1967).
Fischer, et al., *Biol. Psychiat.*, 5:139–147 (1972).
Greenshaw, "B-phenylethylamines: A Functional Role at the Behavioral level," *Neurobiology of the Trace Amines* (Humana Press 1984).
Hamilton, *Br. J. of Social and Clinical Psych.*, 6:278–296 (1967).
Hamilton, *J. Neural. Surg. Psychiat.*, 23:56–61 (1960).
Inwang, et al., *J. Neurochem.*, 20:1469–1473 (1973).
Jackson, *J. Pharm. Pharmacol.*, 24:383–389 (1972).
Jackson and Temple, *Comp. Gen. Pharmacol.*, 1:155–157 (1970).
Karoum, et al., *Biol. Psychiat.*, 19:165–178 (1984).
Mann, et al., *J. Clin. Psychopharmacol.*, 2:54–57 (1982).
Mann and Gershon, *Life Sci.*, 26:877–882 (1980).
Mendis, et al., *Psychopharmacol.*, 73:87–90 (1981).
Mosnaim, et al., *Biol. Psychiat.*, 6:235–257 (1973).
Murphy, et al., "Phenylethylamine, Tyramine and Other Trace Amines in Pateints With Affective Disorders," *Neurobiology of the Trace Amines*, pp. 449–514 (1984).
Nakajima, et al., *J. Pharmacol. Exptl. Therap.*, 143:319–325 (1964).
Philips and Boulton, *J. Neurochem.*, 33:159–167 (1979).
Sabelli, "Clinical Antidepressant Effects of Selegiline and L-phenylalanine Support Mood-regualting Role for Brain 2-phenylethylamine," FASEB, 1991.
Sabelli, *J. Clin. Psych.*, 52(3):137 (1991).
Sabelli, *Proc. Amer. Psychiat. Assoc.*, New Research Program and Abstracts, New York, N.Y. May 12–17, 1990:146.
Sabelli, et al., *Acta Physiol. Pol.*, 24:33–40 (1973).

Sabelli, et al., *Biol. Psychiat.*, 3:273–280 (1971).
Sabelli, et al., *FASEB*, 3(4):A1186 (1989).
Sabelli, et al., *J. Neuropsychiat.*, 1:37–39 (1989).
Sabelli, et al., *Science*, 220:1187–1188 (1983).
Sabelli and Giardina, "Amine Modulation of Affective Behavior," *Chemical Modulation of Brain Function*, pp. 225–259 (Raven Press 1973).
Sabelli and Mosnaim, *Am. J. Psych.*, 131:695–699 (1974).
Varga, et al., *Acta. Med. Acad. Sci. Hung.*, 23:289–295 (1967).
Borison, et al., *Life Sci.*, 17:1331–1344 (1975).
Boulton, *Prog. Neuro–Psychopharmacol. and Biol. Psychiat.*, 15:139–156 (1991).
Fawcett, et al., "CNS Amine Metabolites," *Handbook of Psychiatric Diagnostic Procedures*, vol. 1, Ch. 3, pp. 49–108 (R. C. W. Hall, ed., Spectrum Publications 1984).
Giardina, et al., *Life Sci.*, 12:153–161 (1973).
Kravitz, et al., *J. Am. Osteopathic Assoc.*, 8(1):119–123 (1984).
Paterson, et al., *J. Neurochem.*, 55:1827–1837 (1990).
Sabelli, et al., *Biol. Psychiat.*, 11:481–524 (1976).
Sabelli, et al., *Nature*, 248:144–145 (1974).
Sabelli, et al., "(−)—Trans—Δ⁹—Tetrahydrocannabinol–Induced Increase in Brain 2-Phenylethylamine: Its Possible Role in the Behavioral Effects of Marijuana," *Drug Addition: Neurobiology and Influences on Behavior*, vol. 3, pp. 271–284 (1974).
Vasquez and Sabelli, "Electrophysiological Studies with Δ⁹–Tetrahydrocannabinol," *Drug Addiction: Neurobiology and Influences on Behavior*, vol. 3, pp. 361–374 (J. M. Singh and H. Lal, eds., Stratton 1974).
Vasquez and Sabelli, *Exptl. Neurology*, 46:44–56 (1975).
Davis, et al., *Prog. Neuro–Psychopharmacol. and Biol. Psychiat.*, 15:611–623 (1991).
Durden and Boulton, *J. Neurochem.*, 38:1532–1536 (1982).
Faull, et al., *Psychiat. Res.*, 30:111–118 (1989).
Gusovsky, et al., *Anal. Biochem.*, 136:202–207 (1984).
Mizock, et al., *Arch. Intern. Med.*, 150:443–449 (1990).
Mosnaim, et al., *Clin. Chim. Acta*, 46:407–413 (1973).
Mosnaim, et al., *Biol. Psychiat.*, 8:227–234 (1974).
Sabelli, et al., *J. Clin. Psych.*, 47:66–70 (1986).
Sabelli, et al., *J. Clin. Psychopharmacol.*, 3:268–270 (1983).
Sandler, et al., *Clin. Chim. Acta*, 93:169–171 (1979).
Gray, *Time*, Feb. 15, 1993, pp. 47–51.
Birkmayer, et al., *J. Neural Transmission*, 59:81–87 (1984).
Moja et al., *Biol. Psych.*, 11, 731–42 (1976).
Yang and Neff, *J. Pharmacol. Exptl. Therap.*, 187:365–371 (1973).

(List continued on next page.)

Primary Examiner—Marianne M. Cintins
Assistant Examiner—William R. A. Jarvis
Attorney, Agent, or Firm—Willian Brinks Hofer Gilson & Lione

[57] ABSTRACT

Pharmaceutical compositions for treating psychiatric disorders are provided. The compositions include 2-phenylethylamine ("PEA") and at least one inhibitor of monoamine oxidase B. Methods for the treatment of psychiatric disorders, including depression, using the disclosed pharmaceutical compositions are also provided.

3 Claims, No Drawings

OTHER PUBLICATIONS

Sabelli et al., "Phenylalanine Metabolism in Panic and Other Psychiatric Disorders," Presentation at *VII World Congress of Psychiatry*, Athens, Greece (Sep. 1989).

*Adrenergic Neuron Blocking Agents,* The Pharmacological Basis of Therapeutics, 7th Ed., Ch. 9, pp.204–210 (1985).

Baldessarini, *Drugs and The Treatment of Psychiatric Disorders,* The Pharmacological Basis of Therapeutics, 7th Ed., Ch. 19, pp. 391–447 (1985).

Bianchine, *Drugs For Parkinson's Disease; Centrally Acting Muscle Relaxants,* The Pharmacological Basis of Therapeutics, 7th Ed., Ch. 21, pp. 475–493 (1985).

Weiner, *Norepinephrine, Epinephrine, and the Sympathomi-*

*metic Amines,* The Pharmacological Basis of Therapeutics, 7th Ed., Ch. 8, pp. 138–175 (1985).

METHOD FOR TREATING DEPRESSION

FIELD OF THE INVENTION

The present invention relates to pharmaceutical compositions and their use in the treatment of psychiatric disorders. More particularly, the invention relates to pharmaceutical compositions that include 2-phenylethylamine and at least one inhibitor of monoamine oxidase B, and to methods of using such compositions in the treatment of psychiatric disorders.

BACKGROUND OF THE INVENTION

The need for new antidepressant agents arises from the limited efficacy, slowness of action, and adverse side-effects of many currently available compounds. For instance, some tricyclic antidepressants can cause sedation and atropine-like effects. Still other antidepressants can produce agitation that some persons feel lead them to increase suicidal ideation.

L-phenylalanine is an essential amino acid which is decarboxylated in the brain and peripheral tissues to form 2-phenylethylamine ("PEA"). PEA is then metabolized by monoamine oxidase type B [Yang and Neff, *J. Pharmacol. Exp. Ther.*, 187:365–371 (1973)] to form phenylacetic acid ("PAA"). PEA is normally found stored and metabolized in brain and peripheral tissues. [Sabelli et al., *Acta Physiological Polonica*, 24:33–40 (1973); Inwang et al., *J. Neurochem.*, 20:1469–1473 (1973); Mosnain et al., *Biol. Psychiatry*, 6:235–257 (1973a); Boulton et al., *Br. J. Pharmacol.*, 59:209–214 (1977); Jackson and Temple, *Comp. Gen. Pharmacol.*, 1:155–157 (1970); Phillips et al., *J. Neurochem.*, 33:159–161 (1979); Durden and Phillips, *J. Neurochem.*, 34:1725–1732 (1980)].

It has been reported in the art that depression is not associated with a general PEA deficit in the body. [DeLisi et al., *Psychiatry Research*, 13:193–201 (1984); Karoum et al., *Biological Psychiatry*, 19:165–178 (1984)]. Further, certain clinical observations have led some investigators to conclude that there is no association between PEA and behavioral activation, and that the antidepressant effects of monoamine oxidase inhibitors are not likely to be mediated by increased PEA or associated changes in PEA. [Murphy et al., *Neurobiology of the Trace Amines*, pp. 449–514 (1984)].

Contrary reports concerning PEA have appeared, however, in the psychiatric literature. Fischer and others have reported that a deficit in PEA in the body may be the cause of a form of depressive illness. [Fischer et al., *Acta Physiol. Lat. Am.*, 17:15–21 (1967); Sabelli and Giardina, *Chemical Modulation of Brain Function*, Raven Press, New York, pp. 225–259 (1973); Sabelli and Mosnaim, *Am. J. Psych.*, 131:695–699 (1974); Sabelli et al., *Science*, 220:1187–1188 (1983)]. It is also believed that PEA excess may contribute to some form of mania [Fischer et al., *Biol. Psychiatry*, 5:139–147 (1972)] and schizoaffective psychosis [Sabelli et al., *J. Neuropsychiatry*, 1:37–39 (1989)], and that PEA is an amphetamine-like substance which produces behavioral stimulation when administered to animals. [Nakajima et al., *J. Pharmacol. Exp. Ther.*, 143:319–325 (1964); Fischer et al., *Acta Physiol. Lat. Am.*, 17:15–21 (1967); Jackson, *J. Pharm. Pharmacol.*, 24:383–389 (1972); Sabelli and Giardina, *Chemical Modulation of Brain Function*, New York, Raven Press, pp. 225–59 (1973); Greenshaw, "B-phenylethylamine: A functional role at the behavioral level," *Neurobiology of the Trace Amines*, New Jersey, Humana Press (1984); Sabelli et al., *Biol. Psychiatry*, 3:273–280 (1971)]. This amphetamine-like effect, however, is weak because the PEA is rapidly destroyed by monoamine oxidase.

Karoum and coworkers [*Biol. Psychiatry*, 19:165–178 (1984)] reported the administration of PEA in 4 depressed patients in amounts varying from 200–1600 mg. In each case, though, the administered PEA was quantitatively metabolized to PAA. There were no noticeable pharmacological effects. PEA has also been administered to three patients in combination with phenelzine. [Carlson-Sabelli et al., "Phenylalanine Metabolism in Affective and Other Psychotic Disorders," Presentation at *VII World Congress of Psychiatry*, Athens, Greece (September 1989); Sabelli et al., *FASEB*, 3(4):A1186 (1989)]. This combination ameliorated depression in two patients. This combination is disadvantageous, however, since phenelzine does not selectively inhibit monoamine oxidase B and requires that the patient have a restricted diet.

L-Deprenyl (also known as selegiline) has previously been used as a treatment for Parkinson's disease. Symptoms of depression have also been relieved by treatment with (−) deprenyl at doses of 30 to 60 mg/day that inhibit both the A and B forms of monoamine oxidase. [Varga et al., *Acta. Med. Acad. Sci. Hung.*, 23:289–295 (1967); Mann et al., *Life Sci.*, 26:877–882 (1980); *J. Clin. Psychopharm.*, 2:54–57 (1982)]. When deprenyl is administered at lower doses (5 to 10 mg/day) which selectively inhibit type B monoamine oxidase, no antidepressant effect has been observed. [Mendis et al., *Psychopharmacology*, 73:87–90 (1981)]. However, relief from depression can be obtained when low doses of deprenyl are combined with 250 mg of L-phenylalanine. [Birkmayer et al., *J. Neural Transmission*, 59:81–87 (1984); Knoll et al., U.S. Pat. No. 4,880,883]. Using higher doses of L-phenylalanine (1 to 6 grams/day), it was found that the deprenyl-phenylalanine combination produced recovery from depression in patients resistant to other treatments. [Sabelli, *Proc. of the Amer. psychiat. Assoc.*, New Research Program and Abstracts, New York, N.Y. May 12–17, 1990:146; Sabelli, *J. Clin. Psych.*, 52(3):137 (1991); Sabelli, "Clinical antidepressant effects of selegiline and L-phenylalanine support mood-regulating role for brain 2-phenylethylamine," *FASEB*, 1991].

SUMMARY OF THE INVENTION

In accordance with one embodiment of the invention, there is provided a method of treating a human patient suffering from a psychiatric disorder. The method comprises administering to the patient in a pharmaceutically acceptable carrier an effective amount of 2-phenylethylamine in combination with at least one monoamine oxidase B inhibitor.

In accordance with another embodiment of the invention, there is provided a pharmaceutical composition for use in the treatment of a human patient suffering from a psychiatric disorder. The pharmaceutical composition comprises in a pharmaceutically acceptable carrier an effective amount of 2-phenylethylamine and at least one monoamine oxidase B inhibitor.

The invention is advantageous since administration of 2-phenylethylamine and at least one monoamine oxidase B inhibitor to patients has been shown to provide relatively rapid relief of psychiatric disorder symptoms with a paucity of side effects.

DETAILED DESCRIPTION OF THE INVENTION

The present invention provides methods for treating a human patient suffering from a psychiatric disorder. As used in the present application, the term "psychiatric disorder" is used in a broad sense and refers to conditions in human patients that are usually characterized by symptoms such as depression, anxiety, sleep disturbance, appetite disturbance, hopelessness, helplessness, or low energy. It is contemplated that the methods and compositions of the invention may be used to treat a variety of psychiatric disorders, including but not limited to, affective disorders, panic disorders, Parkinson's disease, Alzheimer's disease, attentional deficit disorders, and adjustment disorders.

In accordance with the inventive methods, an effective amount of 2-phenylethylamine ("PEA") is administered to the patient in combination with at least one monoamine oxidase B inhibitor. As used in the present application, the terms 2-phenylethylamine and PEA refer to the organic chemical compound and its salts, including 2-phenylethylamine chloride. The PEA and monoamine oxidase B inhibitor(s) may be administered to the patient at the time of onset of symptoms characteristic of a psychiatric disorder. Alternatively, the PEA and monoamine oxidase B inhibitor(s) may be administered after symptoms progress, or after other treatment proves unsuccessful.

PEA is a naturally-occurring chemical compound. For instance, PEA is found in the mammalian body and is also present in certain food items such as chocolate. The invention contemplates that the PEA may be extracted or isolated from mammals or plants, or may be prepared synthetically. Techniques for performing such extraction or synthesis are well known to persons skilled in the art. PEA and PEA-hydrochloride are also commercially available and may be purchased from Sigma Chemical Company, St. Louis, Mo.

PEA is preferably administered to the patient in a pharmaceutically-acceptable carrier. Pharmaceutically-acceptable carriers are well known to persons skilled in the art. For instance, suitable carriers for administering PEA include solid forms such as capsules or tablets. Alternatively, the carrier may be a fluid such as water, saline, or buffer. Preferably, the carrier is a solid tablet. It will be apparent to those persons skilled in the art that certain carriers may be more preferable depending upon, for instance, the route of administration and concentration of PEA being administered.

The PEA may be administered to the patient orally or by injection (e.g., intravenous, intraperitoneal, subcutaneous, intramuscular). Preferably, the PEA is administered orally. Effective dosages and schedules for administering PEA may be determined empirically, and making such determinations is within the skill of the art. Applicant has found that a daily dose of from about 0.3 mg to about 1 mg of PEA per kilogram of body weight of the patient is effective for treating depression and other psychiatric disorders. It is understood by those skilled in the art that the dose of PEA that must be administered will vary depending on, for example, the patient which will receive the PEA, the type of disorder, the extent of the symptoms, the route of administration, and the identity of any other drugs or treatment being administered to the patient. Preferably, multiple doses of PEA are administered to the patient daily, and are administered in the morning, mid-day, and early evening hours. Preferably, the PEA is not administered to the patient during night-time hours. Dosages and schedules for administering PEA are further described in the Example below.

As discussed above, PEA is administered to the patient in combination with at least one monoamine oxidase B inhibitor. Compounds which selectively inhibit monoamine oxidase type B are known in the art. Monoamine oxidase B inhibitors contemplated by the present invention include, but are not limited to, selegiline (deprenyl), 3-N-phenylacetylamino-2,5-piperidinedione, pargyline and caroxyazone. The invention contemplates that one type of monoamine oxidase B inhibitor may be administered, or alternatively, a combination of two or more such inhibitors may be administered. Monoamine oxidase B inhibitors are commercially available. For instance, deprenyl may be purchased from Somerset Pharmaceuticals, Inc., Tampa, Fla.

The monoamine oxidase B inhibitor is preferably administered in a pharmaceutically acceptable carrier. The carrier may be in the form of a solid, such as a capsule or tablet, or in liquid form. The monoamine oxidase B inhibitor may be administered to the patient orally or by injection (e.g., intravenous, intraperitoneal, subcutaneous, intramuscular). Preferably, the monoamine oxidase B inhibitor is administered orally. It is within the skill in the art to determine acceptable carriers and proper means of administering the monoamine oxidase B inhibitor. The PEA and monoamine oxidase B inhibitor may be administered by the same means or by different means. For instance, the PEA may be administered to the patient by intravenous injection while the monoamine oxidase B inhibitor is administered orally to the patient.

Effective dosages and schedules for administering PEA are described above. Effective dosages and schedules for administering the monoamine oxidase B inhibitor in combination with PEA may be determined empirically, and making such determinations is within the skill in the art. It will be understood by those persons skilled in this art that the dose of monoamine oxidase B inhibitor administered will vary, depending on, for example, the patient being treated, the type of disorder, and the amount of PEA being administered to the patient. Preferably, deprenyl is administered in daily doses which do not exceed 10 mg/day. Generally, multiple daily doses of monoamine oxidase B inhibitor must be administered in combination with PEA. Dosages and schedules for administering the monoamine oxidase B inhibitor, deprenyl, are described in further detail in the Example below. It is preferable that the monoamine oxidase B inhibitor is administered at the same time as the PEA administration. Administration of the monoamine oxidase B inhibitor and PEA should be continued until health has been restored to the mammal.

EXAMPLE

A clinical study was conducted in the Department of Psychiatry of the School of Medicine of the University of Buenos Aires in Argentina. Ten patients suffering from major depressive disorders were diagnosed according to the Diagnostic and Statistical Manual of the American Psychiatric Association, third edition revised (DSM-IIIR). The symptoms of depression and anxiety were evaluated quantitatively on the basis of three scales widely used in international literature [Hamilton, *J. Neural. Surg. Psychiat.*, 23:56–61 (1960); Beck et al., *Beck Depression Inventory*, New York: Harper & Row Publishers, Inc. 1961; Hamilton, *Journal of Neurological psychiatry*, 23,56–62 (1960); Hamilton, *British Journal of Social and Clinical Psych.*, 6:278–296 (1967)]. All patients were treated with deprenyl 5 mg orally in the morning and early afternoon, and 10 to 20 mg doses of PEA in divided doses of 5–10 mg from 1 to 6 times a day between 6:00 am and 5:00 pm. Unless otherwise noted, the initial dose of PEA was 20 mg per day which was increased to 30 mg per day in the second or third week. The PEA was kept at this dose for 6 weeks, then decreased to 20 mg per day, and then to 10 mg per day for 15 days. The drug trial was then terminated, and patients were revaluated in another 2–3 weeks.

Of the ten patients studied, 6 showed improvement. One patient withdrew from the study after one day. Another patient was terminated from the study because of vertigo. The case studies are described below.

Case 1:

54year old woman with recurrent major depressive episodes with melancholia for 11 years. Her current episode did not respond to treatment that included several tricyclics, monoamine oxidase inhibitors, carbamazepine and lithium. There was no therapeutic response to the combination treatment of deprenyl and PEA.

Case 2:

50year old woman with single episode of a major depressive disorder. The patient had a rapid therapeutic response to the deprenyl/PEA combination, without side effects and without recurrence of depression after termination of the treatment. During the episode, she required Diazepam (5 mg) for insomnia.

Case 3:

33year old single mother with depressive symptoms of 5 year duration. The patient was diagnosed with dysthymia and had a history of recurrent episodes of major depression. The patient became acutely depressed 20 days prior to the start of treatment with prominent retardation, and had homicidal ideation. Her symptoms met the criteria for major depressive disorder and unipolar recurrent. At admission, her Hamilton depression was 17 and her Hamilton anxiety was 24. After 4 days of treatment with 20 mg/day of PEA and deprenyl, she was much improved (Hamilton depression 3; Hamilton anxiety 9); after 4 additional days of treatment with 30 mg/day of PEA and deprenyl, the patient smiled and laughed spontaneously (Hamilton depression 1; Hamilton anxiety 3). During the episode she required Diazepam (5 mg) for insomnia. The only side effect noticed was a decrease in appetite, without a loss of weight. There were no symptoms of abstinence when treatment was terminated, and no further pharmacological treatment was necessary. Psychotherapy was recommended.

Case 4:

62year old woman janitor with a history of recurrent depressions triggered by marital abuse by two alcoholic husbands. Her current depression started 2 months prior to admission when her second husband was found comatose. The patient's prominent symptoms included dysphoria, somatic and subjective anxiety, early morning awakenings, and unresponsiveness to alprazolan. Treatment with 20 mg/day PEA and deprenyl for 5 days reduced depression (Hamilton rating dropped from 13 to 2) and anxiety (Hamilton rating decreased from 11 to 8). When PEA was increased to 30 mg/day for 5 days more, the Hamilton ratings dropped to 1. There were no symptoms of abstinence when treatment was terminated, and no further treatment was necessary.

Case 5:

45year old man with a major depressive disorder, dysthymia, dependent personality and obesity. Patient had a good response to the combination treatment, although the addition of Lorazepan (1 mg) twice a day was required for control of anxiety. In this patient, PEA and deprenyl fully relieved the depression, and there was no significant loss of weight. There were no symptoms of abstinence when treatment was terminated, and no further treatment was necessary.

Case 6:

41year old woman with single episode of depressive illness. The patient received treatment for only one day and then requested to be excluded from the therapeutic trial.

Case 7:

23year old single woman with a history of recurring depression, 4 suicide attempts, and 3 psychiatric hospitalizations. The patient had a childhood history of abuse after death of her mother, and was being treated with corticosteroids for allergies. Her prominent symptoms included insomnia, decreased appetite, loss of weight (10 kg since onset of depression one month prior to admission), somatic anxiety (vertigo), subjective anxiety, headaches, body pains and aches, agitation, and suicidal ideation. This patient was treated with deprenyl plus PEA (20 mg/day) for two days after which she discontinued the treatment complaining of vertigo.

Case 8:

51year old housewife with a history of recurrent depression, multiple hospitalizations, and one serious suicidal attempt. Her depressive episode began 2 years prior to the treatment, separated from the previous episode by a short interval of hypomania followed by a 5 month omission. She had a history of emotional abuse in childhood, and had been diagnosed as a bipolar type 2. Treated with deprenyl and PEA (40 mg/day), the patient experienced a rapid, subjective improvement in ten days, with the Hamilton depression rating dropping from 23 to 7, and the Hamilton anxiety from 11 to 3.

Case 9:

61year old salesman with a history of recurrent depressions and suicidal ideation but no hospitalizations. His prominent symptoms included insomnia, weight gain, lack of motivation, anger, marked decrease in energy, lack of concentration and decrease in memory. This patient experienced a rapid but short-lasting improvement with the treatment (Hamilton depression rating decreasing from 26 to 10 after 10 days of 40 mg/day of PEA), but the improvement was not sustained 10 days later. Treatment was discontinued.

Case 10:

45year old woman entertainer with a history of recurrent depression and several hospitalizations. This episode started one month prior to treatment. Her prominent symptoms included early morning awakening, dysphoria, decreased concentration, motivation and pleasure, increased irritability, anxiety, pessimism, helplessness, and passive suicidal ideation. Her treatment with deprenyl plus PEA (40 mg/day) produced rapid relief with a drop in 10 days of the Hamilton depression rating from 21 to 8.

What is claimed is:

1. A method of treating a human patient suffering from depression, comprising administering to the patient in a pharmaceutically acceptable carrier an effective amount of 2-phenylethylamine in combination with at least one monoamine oxidase B inhibitor.

2. The method of claim 1, wherein said at least one monoamine oxidase B inhibitor is selected from the group consisting of 3-N-phenylacetylamino-2, 5-piperidinedione, deprenyl, and pargyline.

3. The method of claim 2, wherein said at least one monoamine oxidase B inhibitor is deprenyl.

* * * * *